United States Patent [19]
Rosen

[11] Patent Number: 5,228,433
[45] Date of Patent: Jul. 20, 1993

[54] FINGER MOUNTED DENTAL APPLIANCE

[76] Inventor: Robert C. Rosen, P.O. Box 533, Tujunga, Calif. 91043

[21] Appl. No.: 860,547

[22] Filed: Mar. 30, 1992

[51] Int. Cl.$^5$ .............................................. A61H 7/00
[52] U.S. Cl. .................................. 128/62 A; 15/227; 206/369
[58] Field of Search ..................... 128/62 A; 15/227; 206/368, 369

[56] References Cited

U.S. PATENT DOCUMENTS

| | | | |
|---|---|---|---|
| 1,157,413 | 10/1915 | Nesper | 15/227 |
| 1,193,203 | 8/1916 | Taliaferro | 206/369 |
| 2,068,400 | 1/1937 | De Rome | 15/227 |
| 2,092,987 | 9/1937 | Remington | 15/227 |
| 2,101,363 | 12/1937 | De Rome | 128/62 A |
| 2,686,325 | 8/1954 | Silver | 15/227 |
| 2,999,260 | 9/1961 | King | 15/104.94 |
| 3,583,019 | 6/1971 | Conklin, Jr. | 15/227 |
| 3,934,299 | 1/1976 | Regester | 15/227 |
| 4,211,330 | 7/1980 | Strock | 15/227 |
| 4,292,705 | 10/1981 | Stouffer | 15/227 |
| 4,335,731 | 6/1982 | Bora, Jr. | 15/227 |
| 4,449,630 | 5/1984 | Filhol | 206/369 |
| 4,602,650 | 7/1986 | Pipkin | 15/227 |
| 4,893,373 | 1/1990 | Kato | 15/227 |
| 5,010,617 | 4/1991 | Nelson | 15/227 |
| 5,068,941 | 12/1991 | Dunn | 15/227 |

FOREIGN PATENT DOCUMENTS

| | | | |
|---|---|---|---|
| 569115 | 11/1957 | Italy | 15/227 |
| 9388 | 7/1912 | United Kingdom | 15/227 |
| 2043438 | 10/1980 | United Kingdom | 15/227 |

*Primary Examiner*—John J. Wilson
*Attorney, Agent, or Firm*—Sheldon & Mak

[57] ABSTRACT

A tooth and gum appliance that includes a flexible sheet or pad which can carry cleaners, mild abrasives, medicaments or other substances has a miniature hook-loop fastener member at one edge of the pad, the mating fastener member being carried by a tab that extends from the pad opposite the one edge for fastening the appliance about a user's finger. The pad can be formed of cotton loop-woven cloth, and the tab can be a separate strap or an integral portion of the pad. A nested plurality of the polishers can be supplied in a foldable, rectangular carton dispenser having a side slot for access to the fasteners, the tabs protruding from one side of the slot. The dispenser can have a plurality of the slotted, cylindrical cavities spaced about a rotatable drum-shaped holder for permitting the user to select among several configurations of the polisher.

20 Claims, 1 Drawing Sheet

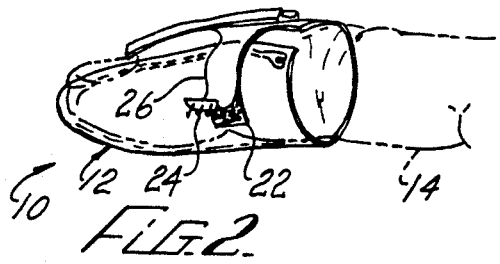
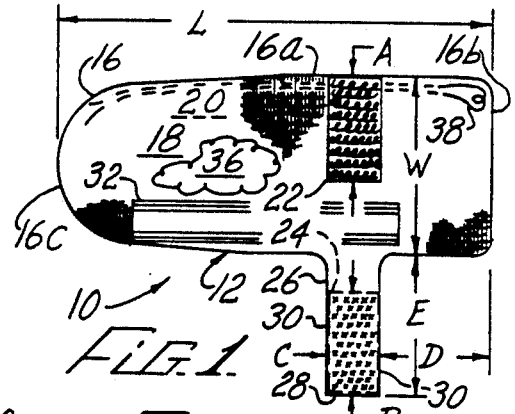
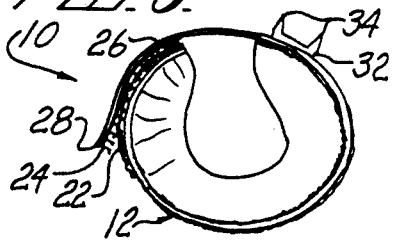
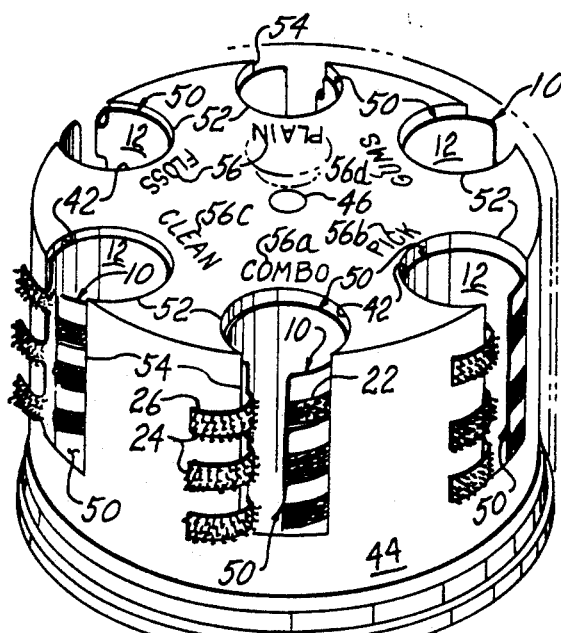
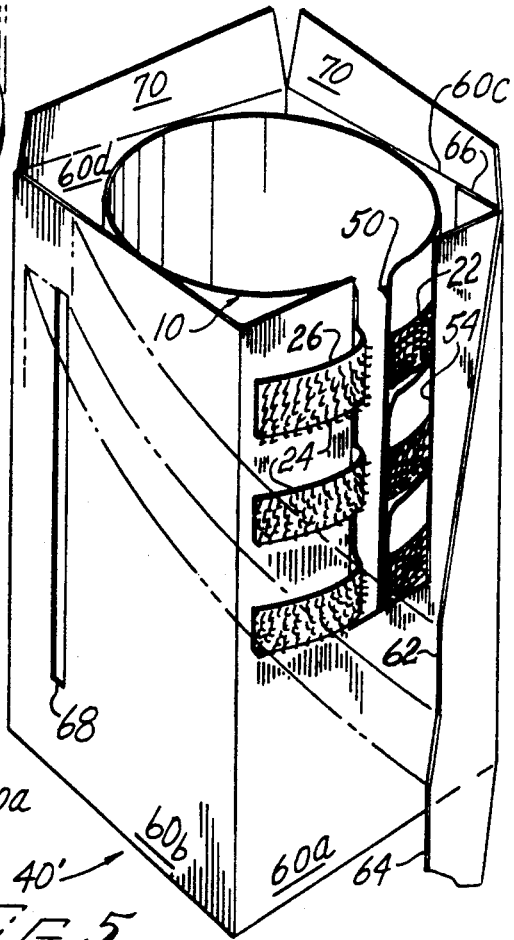
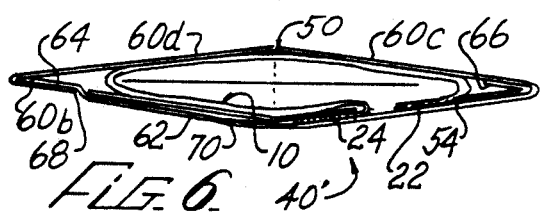
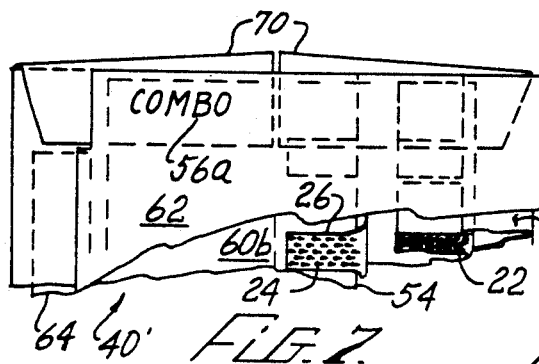

FINGER MOUNTED DENTAL APPLIANCE

BACKGROUND

The present invention relates dental hygiene, and more particularly to devices for facilitating tooth cleaning, gum massaging, and the like.

Traditional toothbrushes are subject to a number of disadvantages. For example, they ordinarily cannot be kept in a sanitary condition following use because ordinary washing does not destroy common bacteria, and sterilizing solutions are dangerous to the user. Also, when it is desired to brush after only a short interval of time, the bristles of ordinary brushes are limp and wet, materially diminishing the effectiveness of the brush. Toothbrushes are also awkward to carry and store following use, being too long for concealment in many clothing pockets, being subject to contamination from the environment, and producing contamination of the environment from moisture and other accumulated matter. Moreover, it is impractical to discard conventional toothbrushes after only a single use, at least for the reason that they are expensive to purchase.

A number of alternatives to the traditional toothbrush have been proposed for avoiding these and other problems. A number of tooth cleaning devices of the prior art are configured for enclosing a portion of the user's finger for cleaning by movement of the finger within the user's mouth, such devices being retained on the finger by the user's thumb gripping a tail portion of the device against the finger. See, for example, U.S. patent No. 2,101,363 to De Rome. It is also known to provide a strand of dental floss with a tooth cleaning device that is received on a user's finger, as disclosed in U.S. Pat. No. 2,999,260 to King.

These devices of the prior art suffer from a number of disadvantages which may account for their not being widely accepted in the marketplace. For example:

1. They are difficult to get fitted to the finger;
2. They are subject to falling off of the finger unless they are retained thereon by continuous thumb pressure;
3. They are expensive to produce, having complex structure or requiring difficult and intricate manufacturing steps; and
4. They are awkward to store and/or difficult to retrieve from a supply of the devices.

Thus there is a need for a dental appliance that is effective for cleaning teeth and massaging gums, that is easy to store and use, and is inexpensive to produce.

SUMMARY

The present invention meets this need by providing a dental appliance for use mounted on a user's finger. In one aspect of the invention, the appliance includes a flexible pad member having front and back faces, first and second side perimeter portions of the pad member extending between a base perimeter portion and a tip perimeter portion, the pad member being wrappable about a portion of the user's finger; a first fastener member fixedly attached to the front face of the pad member; a second fastener member, the second fastener member being connectively engagable with the first fastener member; and means for connecting the second fastener member to the pad member in offset relation to the first fastener member, the fastener members being effective for maintaining the pad member tensioned around the portion of user's finger.

The fastener members can be a mating pair of hook-loop fasteners. The appliance can further include a tab member connected to the pad member and having a tab extremity extending opposite the first side perimeter portion from the second side perimeter portion of the pad member, the second fastener member being connected to the tab portion proximate the tab extremity. The tab member can be formed integrally with the pad member and can include an extension of the back face thereof, the second fastener member being connected to the back face extension.

The fastener members can be spaced between a base perimeter portion and a tip perimeter portion of the pad member for tensioning the pad member about the finger over a major length portion of the pad member. The pad member can have an overall length L between the base perimeter portion and the tip perimeter portion, the length L being between approximately 1 inch and approximately 3 inches, the fastener members having a fastener width C, being spaced from the base perimeter portion by a distance D, the width C being from approximately 0.1 inch to approximately 0.3 inch, the distance D being from approximately 0.2 inch to approximately half of the length L. The pad member can have a body width W between the side perimeter portions, the second fastener member extending an extension distance E from the second side perimeter portion in a direction opposite the first perimeter portion, the distance E plus the width W being from approximately 2.0 inches to approximately 3.5 inches. The distance E can be between approximately 0.4 inch to approximately 0.6 inch. The first fastener member can have a length A and the second fastener has a length B in the direction of the body width W, the fastener lengths A and B each being at least approximately 0.3 inch for adjustably tensioning the pad member about variously sized user's fingers. At least one of the fastener lengths A and B can be at least approximately 0.5 inches.

The appliance can further include a dentifrice coating a portion of the front face of the pad member. The dentifrice can be a tooth cleaner or a medicament for massaging into gums of the user.

Preferably the appliance further includes a pick member for removing foreign matter from between the user's teeth, the pick member being fixably connected to the front face of the pad member. The appliance can further include a length of dental floss removably connected to the pad member.

In a further aspect of the invention, a nested stack of the appliances can be in combination with a dispenser holder for serially dispensing the appliances, the holder having a stack cavity for releasably holding the appliances, the cavity having a finger opening for receiving the user's finger into an innermost one of the appliances, the holder also having a slot formed therein for exposing the fastener members at a side portion of the stack, the innermost of the appliances being tensionably fastenable about the finger for withdrawal of the innermost appliance from the stack on the finger. The holder can have a plurality of the stack cavities formed therein for receiving corresponding stacks of the appliances. The holder can be rotatably mounted to a base member for facilitating access to a selected one of the stack cavities. Preferably a plurality of indicia are fixably located relative to corresponding ones of the stack cavities for identifying selectable variants of the appliances.

The holder can be foldable between open and closed positions, the stack being retained in an open, tubular condition in the open position for receiving the user's finger through the finger opening of the holder, the stack being folded substantially flat and enclosed within the holder in the closed position with the holder being substantially flattened from the open position.

DRAWINGS

These and other features, aspects, and advantages of the present invention will become better understood with reference to the following description, appended claims, and accompanying drawings, where:

FIG. 1 is a plan view of a dental appliance according to the present invention;

FIG. 2 is an oblique elevational perspective view of the appliance of FIG. 1 being worn on a user's finger;

FIG. 3 is a rear elevational view of the appliance of FIG. 1 configured as in FIG. 2;

FIG. 4 is an elevational perspective view showing nested stacks of the appliances of FIG. 1 nested in a multiple compartment dispenser;

FIG. 5 is a perspective elevational view showing a nested stack of the appliances of FIG. 1 nested in an alternatively configured dispenser;

FIG. 6 is a sectional plan view showing the dispenser of FIG. 5 in a flattened configuration; and FIG. 7 is a fragmentary elevational view of a portion of the dispenser of FIG. 6.

DESCRIPTION

The present invention is directed to a dental appliance and dispenser combination that is particularly convenient and effective for facilitating tooth and gum care. With reference to FIGS. 1-3 of the drawings, an appliance 10 includes a pad member 12 for wrapping about a user's finger 14, the pad member 12 having a main perimeter extremity 16, a front surface 18, and a back surface 20. According to the present invention, a first fastener member 22 is affixed to the front surface 18 of the pad member 12, and a second fastener member 24 is affixed to the back surface 20 of the pad member 12, the fastener members 22 and 24 being laterally offset for adjustably securing the appliance 10 with the pad member 12 wrapped about the finger 14 as shown in FIG. 2.

In an exemplary and preferred configuration of the appliance 10, the first fastener member 22 forms a rectangular patch that is located proximate one side portion of the perimeter extremity 16, designated first side margin 16a, the fastener member 22 being spaced from a base or rear margin 16b by a distance D toward a tip or front margin 16c of the perimeter extremity 16, the pad member 12 having an overall length L. The second fastener member 24 is affixed to a tab portion 26 of the pad member 12, the tab portion 26 extending laterally from a second side margin 16d of the pad member 12 by a tab length E, the side margins 16a and 16d defining a body width W of the pad member 12, the pad member 12 also having a thickness T. The second fastener member 24 extends to proximate a free end extremity 28 of the tab portion 26, having a fastener width C that extends to proximate opposite side edge margins 30 of the tab portion 26. As further shown in FIG. 1, the fastener members 22 and 24 are in proximate alignment within the fastener width C for permitting engagement thereof when the pad member 12 is wrapped about the finger 14.

As further shown in FIGS. 1-3, the appliance 10 includes a bladed pick member 32 having upstanding ribs 34, the pick member 32 being affixed to the front surface 18 of the pad member 12 for removing foreign matter from between teeth of the user. Also, a supply of a treatment substance or media 36 is imbedded on at least a portion of the front surface 18 for application by rubbing within the user's mouth during use of the appliance 10. The media 36 can be any suitable tooth cleaning powder or other agent, or an ointment or other medicament for massaging into the user's gums. A further feature of the appliance 10 as shown in FIGS. 1 and 3 is a loop of dental floss 38 that is sewn into the pad member 12 as disclosed and described in U.S. patent No. 2,999,260 to King, discussed above and incorporated herein by this reference.

Suitable fasteners for use as the fastener members 22 and 24 are known as Velcro ® mini hook-loop fasteners that are commercially available from Velcro USA Inc. of Manchester, NH, the first fastener member 22 being a mini hook fastener member, the second fastener member being a mini loop fastener member. Preferably the first fastener member 22 is oriented with the hooked ends facing the free end extremity 28 of the tab portion 26 as best shown in FIG. 3. As shown in FIG. 1, the first fastener 22 has a length A and the second fastener member 24 has a length B in the direction of the body width W. Preferably the lengths A and B are each at least approximately 0.3 inch for providing adjustable tensioning engagement of the fastener members, and for sufficient strength of engagement that the appliance 10 remains effectively supportively tensioned about the user's finger during use thereof. More preferably, at least one of the fastener members 22 and 24 is at least approximately 0.5 inch long for enhancing a range of tensioning adjustment of the pad member 12 about variously sized ones of the finger 14.

Suitable materials for the pad member are one or more layers of loosely woven cloth such as terry cloth, either alone or laminated together with a flexible backing. As shown in FIG. 3, the front surface 18 is formed by a cloth member 12a, the back surface 20 being formed by a plastic sheet member 12b, the members 12a and 12b being connected by any suitable means.

With further reference to FIG. 4, a dispenser 40 for dispensing a supply of the appliances 10 has a plurality of appliance cavities 42 spaced about a generally cylindrically shaped holder member 44, the holder member 44 being rotatably mounted on an upstanding post portion 46 of a supportive base 48. Each of the cavities 42 is generally cylindrical for receiving a nested stack 50 of the appliances 10 and having a top finger opening 52 that is proximate the rear margin 16b of an uppermost (and innermost) one of the nested appliances 10 of the respective stack 50. Each of the fasteners 22 and 24 of the appliances 10 is exposed at a side slot opening of the cavity 42, the tab portions 26 of each pad member 12 being preferably folded outwardly through the slot opening 54 for convenient grasping by the user.

As shown in FIG. 4, each of the cavities 42 can be reserved for a specific variation of the appliances 10, the holder member 44 having indicia 56 thereon for identifying variations of the appliances 10 to be dispensed from corresponding ones of the cavities 42. For example, one of the indicia 56, designated 56a, identifies a combination appliance 10 having the pick member 32, the dental floss 38, and the media 36 providing a cleaning agent as described above in connection with FIGS.

1-3. Another of the indica, designated 56b, identifies counterparts of the appliance 10 having the pick member 32 only, and another of the indica, 56c, identifies counterparts of the appliance 10 having the media 36 supplied as the cleaning agent. A further one of the indica, designated 56d, identifies a counterpart of the appliance 10 having the media 36 as a medicament for use massaging the gums.

In use, the user inserts the finger 14 into the stack 50 for engagement of the uppermost appliance 10 and, while pressing the finger 14 laterally against the cavity 42 proximate the first fastener members 22 for holding the pad members 12 in place, grasps the tab portion 26 of the uppermost appliance 10, tightening the pad member 12 about the finger 14 and simultaneously connecting the fasteners 22 and 24. Thus the uppermost of the appliances 10 is pulled slightly inwardly from the cavity 42 and from the others of the appliances 10 of the stack 50 so that the finger 14, together with the uppermost appliance 10 may be withdrawn from the stack 50.

With further reference to FIGS. 5-7, another preferred configuration of the dispenser 40, designated 40', is collapsible for conveniently carrying one of the nested stacks 50 in a pocket of the user's clothing (not shown). In particular, the dispenser 40' forms a rectangular tubular member 58 of a suitably stiff material such as cardboard, having an integrally connected front panel 60a, side panels 60b and 60c, and a rear panel 60d. The dispenser 40' also includes a cover panel 62 that extends forwardly from the side panel 60c and having a leftwardly extending cover tab 64, a panel tab 66 connecting the front panel 60a to the forward extremity of the side panel 60c. The front panel 60a is also slotted for forming a counterpart of the side slot opening 54, the tops of the panels 60 forming a counterpart of the finger opening 52 when the dispenser 40' is open as shown in FIG. 5.

In further accordance with the present invention, the dispenser 40' can be flattened and closed, as shown in FIGS. 6 and 7, with the cover tab 64 engaging a tab slot 68 of the side panel 60b. As further shown in FIGS. 5 and 7, a pair of end tabs 70 form upper and lower extensions of the rear panel 60d and side panel 60c, the end tabs 70 being folded over the front panel 60a, the side panel 60b being held in place by the cover tab 62 in its closed position as shown in FIG. 7. Thus the nested stack 50 is flattened and enclosed within the dispenser 40' for convenient transport and storage until use of one of the appliances 10 is desired. The dispenser 40' can also be provided with a counterpart of the indicia 56 as shown at 56a in FIG. 7. Accordingly, convenient selection from various configurations of the appliance 10 can be made from corresponding counterparts of the dispenser 40'.

Although the present invention has been described in considerable detail with reference to certain preferred versions thereof, other versions are possible. For example, a variety of materials and textures can be used for the pad member 12, including soft rubber for massaging the gums and for cleaning between the teeth. The media 36 can include various tooth and gum medicines such as antiseptics, chlorophyll, and numbing agents, and coloring agents such as whiteners. The pick member 32 and the ribs 34 can be variously placed and oriented on the pad member 12, and soft wood can be used for the ribs 34 and elsewhere for cleaning between the teeth. The appliance 10 can be used in care of one's own teeth and gums or those of another.

The dispenser 40 can be provided with the cavities 42 of the holder member 44 formed for receiving corresponding ones of the single stack dispensers 40'. Therefore, the spirit and scope of the appended claims should not necessarily be limited to the description of the preferred versions contained herein.

What is claimed is:

1. A dental appliance for use mounted on a user's finger, comprising:
   (a) a flexible sheet pad member having front and back faces, first and second side perimeter portions of the pad member extending between a base perimeter portion and a tip perimeter portion, the pad member being wrappable about a portion of the user's finger;
   (b) a first fastener member fixedly attached to the front face of the pad member;
   (c) a second fastener member, the second fastener member being connectively engagable with the first fastener member when the fastener members are pressed together;
   (d) means for connecting the second fastener member to the pad member in offset relation to the first fastener member, the fastener members being effective for maintaining the pad member tensioned around the portion of user's finger; and
   (e) a tab member connected to the pad member and having a tab extremity extending opposite the first side perimeter portion from the second side perimeter portion of the pad member, the second fastener member being connected to the tab portion proximate the tab extremity.

2. The appliance of claim 1, wherein the fastener members are a mating pair of hook-loop fasteners.

3. The appliance of claim 1, wherein the tab member is formed integrally with the pad member and including an extension of the back face thereof, the second fastener member being connected to the back face extension.

4. The appliance of claim 1, wherein the fastener members are spaced between a base perimeter portion and a tip perimeter portion of the pad member for tensioning the pad member about the finger over a major length portion of the pad member.

5. The appliance of claim 4, wherein the pad member has an overall length L between the base perimeter portion and the tip perimeter portion, the length L being between approximately 1 inch and approximately 3 inches, the fastener members having a fastener width C, being spaced from the base perimeter portion by a distance D, the width C being from approximately 0.1 inch to approximately 0.3 inch, the distance D being from approximately 0.2 inch to approximately half of the length L.

6. The appliance of claim 5, wherein the pad member has a body width W between the side perimeter portions, the second fastener member extending an extension distance E from the second side perimeter portion in a direction opposite the first perimeter portion, the distance E plus the width W being from approximately 2.0 inches to approximately 3.5 inches.

7. The appliance of claim 6, wherein the distance E is from approximately 0.4 inch to approximately 0.6 inch.

8. The appliance of claim 6, wherein the first fastener member has a length A and the second fastener has a length B in the direction of the body width W, the fastener lengths A and B each being at least approximately 0.3 inch for adjustably tensioning the pad member about variously sized user's fingers.

9. The appliance of claim 8, wherein at least one of the fastener lengths A and B is at least approximately 0.5 inches.

10. The appliance of claim 1, further comprising a dentifrice coating a portion of the front face of the pad member.

11. The appliance of claim 10, wherein the dentifrice is a tooth cleaner.

12. The appliance of claim 10, wherein the dentifrice is a medicament for massaging into gums of the user.

13. The appliance of claim 1, further comprising a pick member for removing foreign matter from between the user's teeth, the pick member being fixably connected to the front face of the pad member.

14. The appliance of claim 1, further comprising a length of dental floss removably connected to the pad member.

15. A dental appliance for use mounted on a user's finger, comprising:
   (a) a flexible sheet pad member having front and back faces, first and second side perimeter portions of the pad member extending between a base perimeter portion and a tip perimeter portion, the pad member being wrappable about a portion of the user's finger;
   (b) a first fastener member fixedly attached to the front face of the pad member;
   (c) a second fastener member, the second fastener member being connectively engagable with the first fastener member when the fastener members are pressed together; and
   (d) means or connecting the second fastener member to the pad member in offset relation to the first fastener member, the fastener members being effective for maintaining the pad member tensioned around the portion of user's finger,
   a plurality of appliances nested in a stack and in combination with a dispenser holder for serially dispensing the appliances, the holder having a stack cavity for releasably holding the appliances, the cavity having a finger opening for receiving the user's finger into an innermost one of the appliances, the holder also having a slot formed therein for exposing the fastener members at a side portion of the stack,
   the innermost of the appliances being tensionably fastenable about the finger for withdrawal of the innermost appliance from the stack on the finger.

16. The combination of claim 15, wherein the holder has a plurality of the stack cavities formed therein for receiving corresponding stacks of the appliances.

17. The combination of claim 16, wherein the holder is rotatably mounted to a base member for facilitating access to a selected one of the stack cavities.

18. The combination of claim 16, further comprising a plurality of indicia fixably located relative to corresponding ones of the stack cavities for identifying selectable variants of the appliances.

19. The appliance of claim 15, wherein the holder is foldable between open and closed positions, the stack being retained in an open, tubular condition in the open position for receiving the user's finger through the finger opening of the holder, the stack being folded substantially flat and enclosed within the holder in the closed position with the holder being substantially flattened from the open position.

20. A dental appliance for use mounted on a user's finger, comprising:
   (a) a flexible sheet pad member having front and back faces, first and second side perimeter portions of the pad member extending between a base perimeter portion and a tip perimeter portion, the pad member having an overall length L of between approximately 1 inch and approximately 3 inches between the base perimeter portion and the tip perimeter portion, and a body width W between the side perimeter portions, the pad member being wrappable about a portion of the user's finger;
   (b) a first fastener member fixedly attached to the front face of the pad member;
   (c) a second fastener member, the second fastener member being connectively engagable with the first fastener member, the fastener members being a mating pair of hookloop fasteners and having a width C, the first fastener member also having a length A, the second fastener member having a length B;
   (d) a tab member formed integrally with the pad member and having a tab extremity extending opposite the first side perimeter portion from the second side perimeter portion of the pad member, the second fastener member being connected to the tab portion in offset relation to the first fastener member proximate the tab extremity on an extension of the back face of the pad member, the fastener members being spaced from the base perimeter portion toward the tip perimeter portion of the pad member by a distance D of from approximately 0.2 inch to approximately half of the length L for tensioning the pad member about the finger over a major length portion of the pad member, the width C being from approximately 0.1 inch to approximately 0.3 inch, the second fastener member extending an extension distance E from the second side perimeter portion in a direction opposite the first perimeter portion, the distance E plus the width W being from approximately 2.0 inches to approximately 3.5 inches, the fastener lengths A and B each being at least approximately 0.3 inch, at least one of the fastener lengths being at least approximately 0.5 inches in the direction of the body width W for adjustably tensioning the pad member about variously sized user's fingers.

* * * * *